US009339264B2

(12) United States Patent
Piech et al.

(10) Patent No.: US 9,339,264 B2
(45) Date of Patent: May 17, 2016

(54) PORT ACCESS VISUALIZATION PLATFORM

(75) Inventors: David Keith Piech, Belle Mead, NJ (US); Deepthi Jampala, Cary, NC (US); Vihar C. Surti, Winston-Salem, NC (US); Michelle D. Martinez, Winston-Salem, NC (US); John Crowder Sigmon, Jr., Greensboro, NC (US); David R. Wagner, Clemmons, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1068 days.

(21) Appl. No.: 13/408,640

(22) Filed: Feb. 29, 2012

(65) Prior Publication Data

US 2012/0209070 A1 Aug. 16, 2012

Related U.S. Application Data

(63) Continuation-in-part of application No. 12/896,373, filed on Oct. 1, 2010, now Pat. No. 9,232,962.

(51) Int. Cl.
*A61B 1/32* (2006.01)
*A61B 17/02* (2006.01)
(Continued)

(52) U.S. Cl.
CPC ............ *A61B 17/0293* (2013.01); *A61B 1/0056* (2013.01); *A61B 1/00154* (2013.01); *A61B 1/3132* (2013.01); *A61B 1/05* (2013.01); *A61B 17/3423* (2013.01); *A61B 19/5212* (2013.01); *A61B 2017/00283* (2013.01); *A61B 2017/00305* (2013.01); *A61B 2017/3445* (2013.01)

(58) Field of Classification Search
CPC .. A61B 2017/003; A61B 1/05; A61B 1/0056; A61B 1/00154; A61B 1/00135
USPC .................................. 600/201–206, 208, 210
See application file for complete search history.

(56) References Cited

U.S. PATENT DOCUMENTS 3,677,262 A 7/1972 Zukowski
3,690,775 A * 9/1972 Cousins ...................... 356/241.4
(Continued)

FOREIGN PATENT DOCUMENTS

GB 2031281 4/1980
GB 2052996 2/1981

OTHER PUBLICATIONS

International Search Report/Written Opinion for PCT/US2010/051111 (Jan. 1, 2011).
(Continued)

*Primary Examiner* — Mary Hoffman
(74) *Attorney, Agent, or Firm* — Brinks Gilson & Lione

(57) ABSTRACT

A medical system generally comprises a camera head, a beam, and a guide sheath. The camera head is connected to the beam which is bendable in a first direction and resists bending in a second direction opposite the first direction. The guide sheath slidably receives the beam, the beam extending through a distal end of the guide sheath such that the camera head projects from the distal end of the guide sheath. The guide sheath includes first and second sheath portions, and in an operative configuration the first sheath portion is angled relative to the second sheath portion to define a first bend. The beam is oriented relative to the guide sheath such that, as the beam is slid relative to guide sheath, the beam bends in the first direction through the first bend, and a projecting portion of the beam resists bending in the second direction.

29 Claims, 7 Drawing Sheets

(51) Int. Cl.
*A61B 1/00* (2006.01)
*A61B 1/005* (2006.01)
*A61B 1/313* (2006.01)
*A61B 17/34* (2006.01)
*A61B 19/00* (2006.01)
*A61B 17/00* (2006.01)
*A61B 1/05* (2006.01)

(56) References Cited

U.S. PATENT DOCUMENTS

| | | | |
|---|---|---|---|
| 3,778,170 A * | 12/1973 | Howell et al. | 356/241.4 |
| 4,222,382 A * | 9/1980 | Antonsson et al. | 606/100 |
| 4,254,763 A | 3/1981 | McCready et al. | |
| 4,640,124 A * | 2/1987 | Diener et al. | 73/114.01 |
| 4,911,148 A * | 3/1990 | Sosnowski et al. | 600/136 |
| 5,133,336 A * | 7/1992 | Savitt et al. | 600/132 |
| 5,522,788 A * | 6/1996 | Kuzmak | 600/141 |
| 5,643,221 A * | 7/1997 | Bullard | 604/194 |
| 5,976,075 A * | 11/1999 | Beane et al. | 600/146 |
| 6,416,469 B1 | 7/2002 | Phung et al. | |
| 6,539,942 B2 * | 4/2003 | Schwartz et al. | 128/207.14 |
| 7,553,277 B2 * | 6/2009 | Hoefig et al. | 600/173 |
| 7,575,548 B2 | 8/2009 | Takemoto et al. | |
| 7,658,738 B2 | 2/2010 | Nobis et al. | |
| 7,717,847 B2 | 5/2010 | Smith | |
| 7,749,198 B2 | 7/2010 | Smith | |
| 7,753,901 B2 | 7/2010 | Piskun et al. | |
| 7,762,990 B2 | 7/2010 | Judson et al. | |
| 7,766,810 B2 | 8/2010 | Ohdaira | |
| 7,798,998 B2 | 9/2010 | Thompson et al. | |
| 7,806,870 B2 | 10/2010 | Mastri et al. | |
| 7,815,565 B2 | 10/2010 | Stefanchik et al. | |
| 7,955,254 B2 * | 6/2011 | Hanke | 600/173 |
| 7,963,976 B2 * | 6/2011 | Goldfarb et al. | 606/143 |
| 8,616,526 B2 * | 12/2013 | Rubin et al. | 254/134.3 FT |
| 2004/0230095 A1 | 11/2004 | Stefanchik et al. | |
| 2005/0096508 A1 | 5/2005 | Valentini et al. | |
| 2006/0004369 A1 | 1/2006 | Patel et al. | |
| 2007/0055108 A1 | 3/2007 | Taylor et al. | |
| 2007/0167682 A1 * | 7/2007 | Goldfarb et al. | 600/114 |
| 2007/0244362 A1 * | 10/2007 | El-Hachem | 600/144 |
| 2008/0051802 A1 * | 2/2008 | Schostek et al. | 606/108 |
| 2008/0132758 A1 * | 6/2008 | Stefanchik et al. | 600/104 |
| 2008/0208001 A1 * | 8/2008 | Hadani | 600/128 |
| 2008/0287741 A1 * | 11/2008 | Ostrovsky et al. | 600/141 |
| 2008/0287743 A1 | 11/2008 | Smith et al. | |
| 2008/0300547 A1 | 12/2008 | Bakos | |
| 2008/0319258 A1 | 12/2008 | Thompson | |
| 2009/0054728 A1 | 2/2009 | Trusty | |
| 2009/0143643 A1 | 6/2009 | Weitzner et al. | |
| 2009/0149714 A1 | 6/2009 | Bonadio | |
| 2009/0171151 A1 * | 7/2009 | Choset et al. | 600/114 |
| 2009/0192465 A1 | 7/2009 | Smith | |
| 2009/0259172 A1 | 10/2009 | Yamaoka et al. | |
| 2009/0275798 A1 | 11/2009 | Naito | |
| 2009/0275967 A1 | 11/2009 | Stokes et al. | |
| 2009/0276055 A1 | 11/2009 | Harris et al. | |
| 2010/0010298 A1 | 1/2010 | Bakos et al. | |
| 2010/0010299 A1 | 1/2010 | Bakos et al. | |
| 2010/0036200 A1 | 2/2010 | Okada | |
| 2010/0042078 A1 | 2/2010 | Okada | |
| 2010/0049162 A1 | 2/2010 | Hameed | |
| 2010/0063358 A1 | 3/2010 | Kessler | |
| 2010/0063359 A1 | 3/2010 | Okoniewski | |
| 2010/0081863 A1 | 4/2010 | Hess et al. | |
| 2010/0081864 A1 | 4/2010 | Hess et al. | |
| 2010/0081871 A1 | 4/2010 | Widenhouse et al. | |
| 2010/0081877 A1 | 4/2010 | Vakharia | |
| 2010/0081880 A1 | 4/2010 | Widenhouse et al. | |
| 2010/0081881 A1 | 4/2010 | Murray et al. | |
| 2010/0081882 A1 | 4/2010 | Hess et al. | |
| 2010/0081883 A1 | 4/2010 | Murray et al. | |
| 2010/0081995 A1 | 4/2010 | Widenhouse et al. | |
| 2010/0094284 A1 | 4/2010 | Mikkaichi et al. | |
| 2010/0114033 A1 | 5/2010 | Fischvogt | |
| 2010/0130817 A1 | 5/2010 | Conlon | |
| 2010/0152539 A1 | 6/2010 | Ghabrial et al. | |
| 2010/0160729 A1 | 6/2010 | Smith et al. | |
| 2010/0160735 A1 | 6/2010 | Bakos | |
| 2010/0168519 A1 | 7/2010 | Matsuo | |
| 2010/0168522 A1 | 7/2010 | Wenchell et al. | |
| 2010/0210912 A1 | 8/2010 | Bettuchi | |
| 2010/0211012 A1 | 8/2010 | Hathaway et al. | |
| 2010/0211084 A1 | 8/2010 | Fowler | |
| 2010/0222643 A1 | 9/2010 | Piskun et al. | |
| 2010/0222747 A1 | 9/2010 | Wenchell et al. | |
| 2010/0228090 A1 | 9/2010 | Weisenburgh, II et al. | |
| 2010/0228091 A1 | 9/2010 | Widenhouse et al. | |
| 2010/0228092 A1 | 9/2010 | Ortiz et al. | |
| 2010/0228094 A1 | 9/2010 | Ortiz et al. | |
| 2010/0228096 A1 | 9/2010 | Weisenburgh, II et al. | |
| 2010/0228198 A1 | 9/2010 | Widenhouse et al. | |
| 2010/0234688 A1 | 9/2010 | Carter | |
| 2010/0234806 A1 | 9/2010 | Bettuchi et al. | |
| 2010/0240960 A1 | 9/2010 | Richard | |
| 2010/0241078 A1 | 9/2010 | Barnes | |
| 2010/0249498 A1 | 9/2010 | Wingardner et al. | |
| 2010/0249515 A1 | 9/2010 | Hudon et al. | |
| 2010/0249525 A1 | 9/2010 | Shelton, IV et al. | |
| 2010/0249708 A1 | 9/2010 | Bettuchi et al. | |
| 2010/0249709 A1 | 9/2010 | Fischvogt | |
| 2010/0249711 A1 | 9/2010 | Fischvogt | |
| 2010/0249810 A1 | 9/2010 | Taylor | |
| 2010/0256447 A1 | 10/2010 | Dubi et al. | |
| 2010/0256453 A1 | 10/2010 | Hammond et al. | |
| 2010/0256566 A1 | 10/2010 | Smith | |
| 2010/0256567 A1 | 10/2010 | Smith | |
| 2010/0256636 A1 | 10/2010 | Fernandez et al. | |
| 2010/0261962 A1 | 10/2010 | Friedberg | |
| 2010/0261969 A1 | 10/2010 | Fischvogt et al. | |
| 2010/0261974 A1 * | 10/2010 | Shelton et al. | 600/208 |
| 2010/0261975 A1 | 10/2010 | Huey et al. | |
| 2010/0261976 A1 | 10/2010 | Horton | |
| 2010/0262080 A1 | 10/2010 | Shelton, IV et al. | |
| 2010/0268162 A1 | 10/2010 | Shelton, IV et al. | |
| 2010/0274093 A1 | 10/2010 | Shelton, IV | |
| 2010/0280327 A1 | 11/2010 | Nobis et al. | |
| 2010/0286478 A1 | 11/2010 | Ewers et al. | |
| 2010/0286483 A1 | 11/2010 | Bettuchi et al. | |
| 2010/0286484 A1 | 11/2010 | Stellon et al. | |
| 2010/0286706 A1 | 11/2010 | Judson et al. | |
| 2010/0298646 A1 | 11/2010 | Stellon et al. | |
| 2010/0298775 A1 | 11/2010 | Berry et al. | |
| 2010/0312060 A1 | 12/2010 | Widenhouse et al. | |
| 2010/0312061 A1 | 12/2010 | Hess et al. | |
| 2010/0312063 A1 | 12/2010 | Hess et al. | |
| 2010/0312065 A1 | 12/2010 | Shelton, IV et al. | |
| 2011/0021877 A1 | 1/2011 | Fortier et al. | |
| 2011/0028793 A1 | 2/2011 | Martin et al. | |
| 2011/0028794 A1 | 2/2011 | Widenhouse et al. | |
| 2011/0028795 A1 | 2/2011 | Hotter | |
| 2011/0028891 A1 | 2/2011 | Okoniewski | |
| 2011/0034778 A1 | 2/2011 | Kleyman | |
| 2011/0034935 A1 | 2/2011 | Kleyman | |
| 2011/0034947 A1 | 2/2011 | Kleyman | |
| 2011/0144590 A1 * | 6/2011 | Sakai et al. | 604/167.01 |
| 2011/0196204 A1 * | 8/2011 | Setty et al. | 600/120 |
| 2011/0257637 A1 * | 10/2011 | Timmerman | 606/1 |
| 2012/0312103 A1 * | 12/2012 | Hannott et al. | 73/865.8 |

OTHER PUBLICATIONS

Office Action dated Apr. 11, 2012 in related application.
Office Action dated Oct. 26, 2012 in related application.
Final Office Action dated Mar. 14, 2013 in related application.
Office Action dated Nov. 21, 2014 in related application.
Final Office Action dated Mar. 10, 2015 in related application.
Office Action dated Jun. 2, 2015 in related application.

* cited by examiner

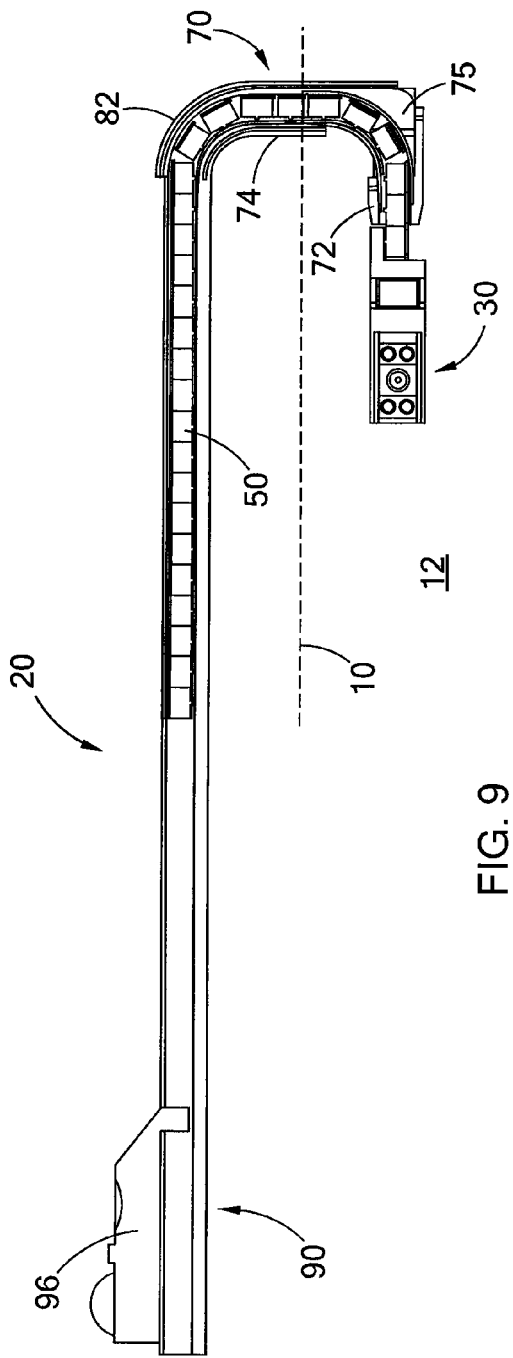
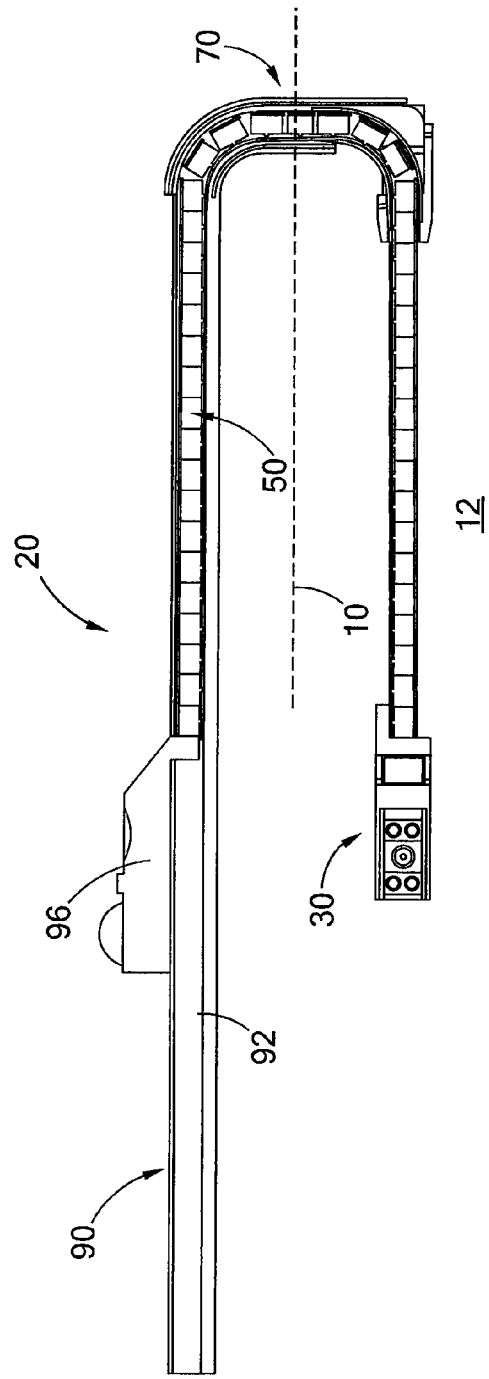

PORT ACCESS VISUALIZATION PLATFORM

CROSS-REFERENCE TO RELATED APPLICATIONS

This application is a continuation-in-part of U.S. application Ser. No. 12/896,373 filed Oct. 1, 2010, entitled "APPARATUS FOR SINGLE PORT ACCESS", the entire contents of which are incorporated herein by reference.

FIELD OF THE INVENTION

The present invention relates generally to medical devices and systems for use with laparoscopic procedures, and more particularly to apparatus for guiding medical instruments during such procedures.

BACKGROUND

Traditional laparoscopic procedures involve the formation of puncture sites through the skin and related tissue layers to provide access to an internal structure within a bodily cavity. Upon formation of a puncture site, the natural elasticity of the tissue tends to close the opening, and thus a port is utilized to hold the site open. For example, a trocar port is device having a tubular configuration defining a port opening and having a configuration that engages the tissue to hold the site open.

Multiple puncture sites, for example three or more, are provided in the desired area so that multiple instruments may be used for the particular laparoscopic procedure, as well as to allow for triangulation of the target structure. For example, a laparoscope or other visualization system may utilize one port, while a grasper or other tissue manipulator is used with the second port in conjunction with a cutting or suturing device utilized through the third port. While laparoscopic procedures are less invasive when compared to traditional open surgery, these procedures still leave multiple scars.

BRIEF SUMMARY OF THE INVENTION

One embodiment of a medical system, for use intracorporeally to assist in surgical procedures beneath a tissue layer, generally comprises a camera head, a beam, and a guide sheath. The camera head has a camera attached thereto, and the beam has a distal end attached to the camera head. The beam is bendable in a first direction and resists bending in a second direction opposite the first direction. The guide sheath slidably receives the beam, the beam extending through a distal end of the guide sheath such that the camera head projects from the distal end of the guide sheath. The guide sheath includes a first sheath portion defining a first axis and a second sheath portion defining a second axis, the guide sheath having an operative configuration wherein the first sheath portion is angled relative to the second sheath portion to define a first bend. The beam is oriented relative to the guide sheath such that, as the beam is slid relative to guide sheath, the beam bends in the first direction through the first bend, and a projecting portion of the beam projecting from the distal end of the guide sheath resists bending in the second direction. A port may optionally be provided as part of the system, and the components are sized such that the first sheath portion may pass through the port with the beam extending from a first side of the tissue layer to a second side of the tissue layer opposite the first side.

According to more detailed aspects of this embodiment of the medical system, the beam sufficiently resists bending such that it does not bend under its own weight and the weight of the camera head. Preferably the beam sufficiently resists bending such that the projecting portion of the beam defines a beam axis extending linearly from the distal end of the guide sheath. The beam may be formed by a plurality of links connected together for relative rotation between adjacent links. In one variation, the links are connected by bendable strip on a first side of each link. In another variation, the links are hinged together at their ends, the ends defining an end surface that is structured to permit rotation of adjacent links relative to each other in the first direction, but restricts rotation of adjacent links towards each other in the second direction. The beam is preferably hollow to define a passageway extending to the distal end of the beam, and the system further includes one or more control wires extending through the passageway and operatively connected to the camera head.

According to further detailed aspects of this embodiment of the medical system, the first bend is formed by the first sheath portion being angled about 90 degrees relative to the second sheath portion. The first sheath portion is rotatably attached to the second sheath portion. As such, the guide sheath has an introduction configuration wherein the first sheath portion is generally parallel to the second sheath portion. Preferably, the first sheath portion is operable to rotate relative to the second sheath portion over an arc spanning about 90 to about 180 degrees. The guide sheath may further include a third sheath section angled relative to second section to define a second bend. The second bend may be at a fixed angle, such as 90 degrees. Preferably, the first and second bend are oriented in the operative configuration to bend the beam over 180 degrees such that a proximal beam portion is about parallel to a distal beam portion.

According to still further detailed aspects of this embodiment of the medical system, the camera head includes a proximal head portion fixed to the beam and a distal head portion rotatably attached to the proximal head portion. The distal head portion may rotate about a pivot axis such that the distal head portion is angled relative to the proximal head portion. Here, the pivot axis is perpendicular to a longitudinal axis of a projecting portion of the beam that projects from the guide sheath. The pivot axis may also be about parallel to a longitudinal axis of a projecting portion of the beam that projects from the guide sheath. In a preferred variation, the camera head further includes an intermediate head portion interconnecting the proximal and distal head portions, wherein the intermediate head portion is rotatable relative to one of the proximal and distal head portions about a first pivot axis such that the distal head portion is angled relative to the proximal head portion, and wherein the intermediate head portion is rotatable relative to other of the proximal and distal head portions about a second pivot axis that is about parallel to a longitudinal axis of a projecting portion of the beam that projects from the guide sheath.

According to yet further detailed aspects of this embodiment of the medical system, the medical system may further comprise a handle attached to the guide sheath. The handle preferably includes a handle housing and a control slider slidably attached thereto, the control slider attached to the beam for translation of the beam through the guide sheath to position the camera head relative to the guide sheath. The handle is operatively connected to one or more control wires, such as a sheath control wire operatively connected to the first sheath section, one or more camera control wire extending through the passageway of the beam operatively connected to the camera head. The camera control wires may be mechanical, electrical and/or optical control wires for operation of the camera head. Any of these control wires preferably extend through the passageway of the beam

BRIEF DESCRIPTION OF THE DRAWINGS

FIGS. 8-10 are cross-sectional views of the medical system depicted in FIGS. 1-3, showing steps of operating the medical system;

DETAILED DESCRIPTION OF THE INVENTION

The terms "proximal" and "distal" as used herein are intended to have a reference point relative to the user. Specifically, throughout the specification, the terms "distal" and "distally" shall denote a position, direction, or orientation that is generally away from the user, and the terms "proximal" and "proximally" shall denote a position, direction, or orientation that is generally towards the user.

Figure 1:
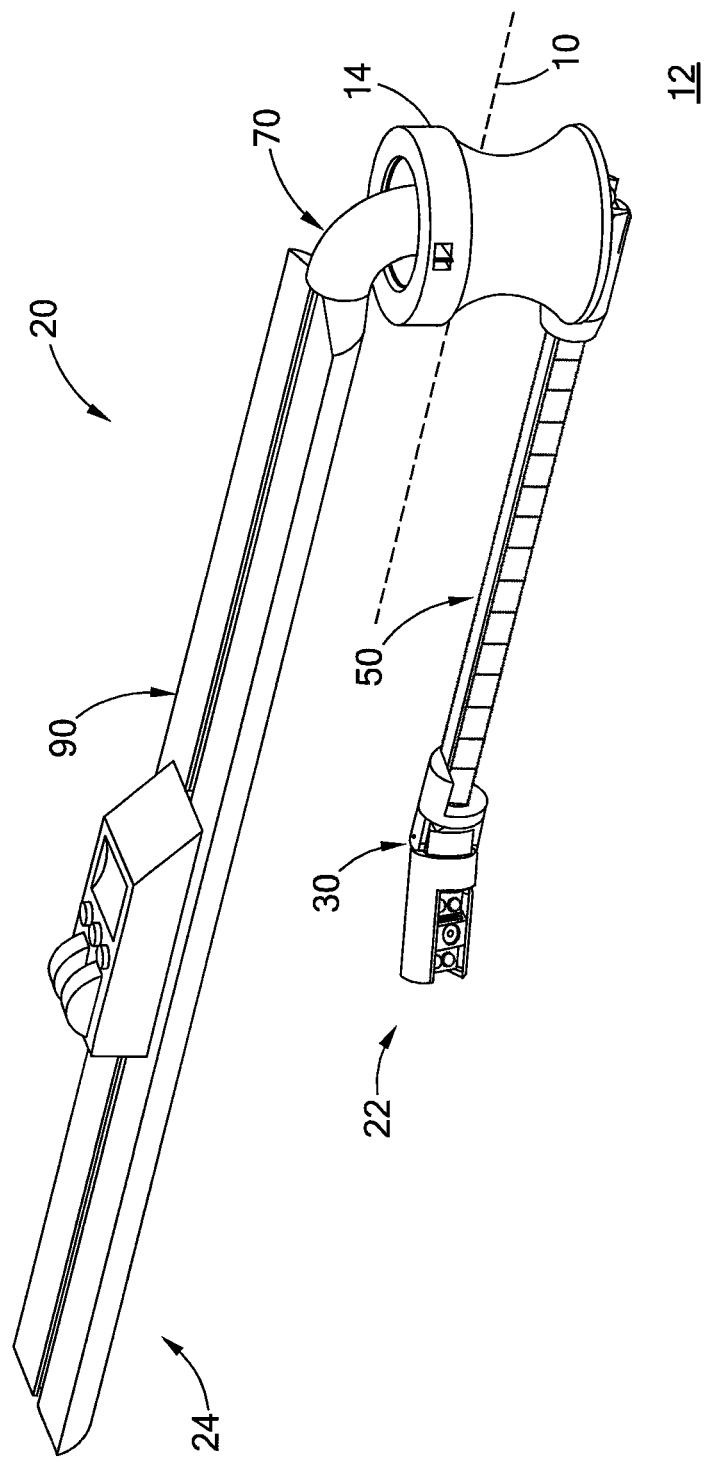
FIG. 1 is a perspective view of the medical system constructed in accordance with the teachings of the present invention.
Figure 2:
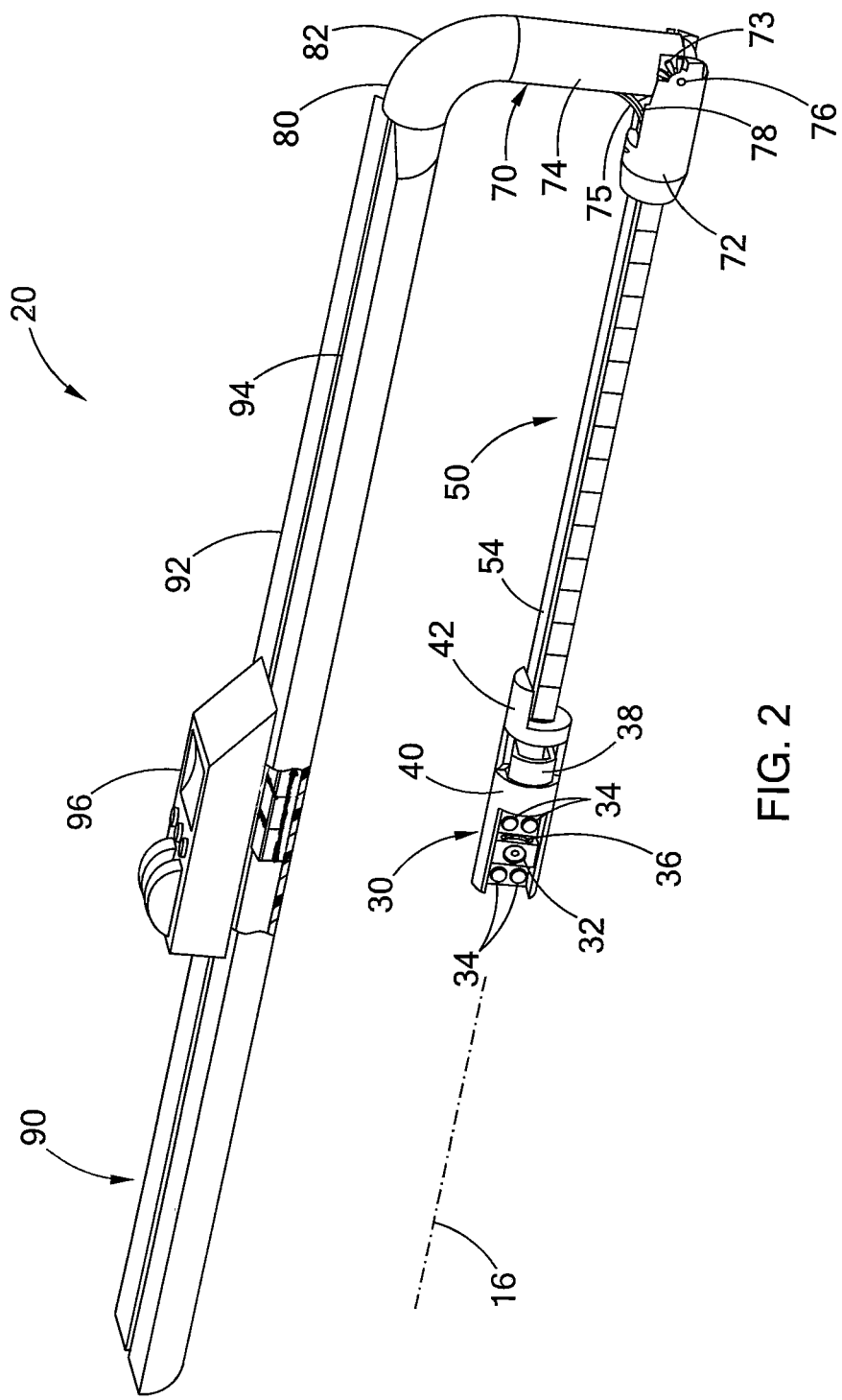
FIG. 2 is another perspective view, partially in cross-section, of the medical system depicted in FIG. 1.
Figure 3:
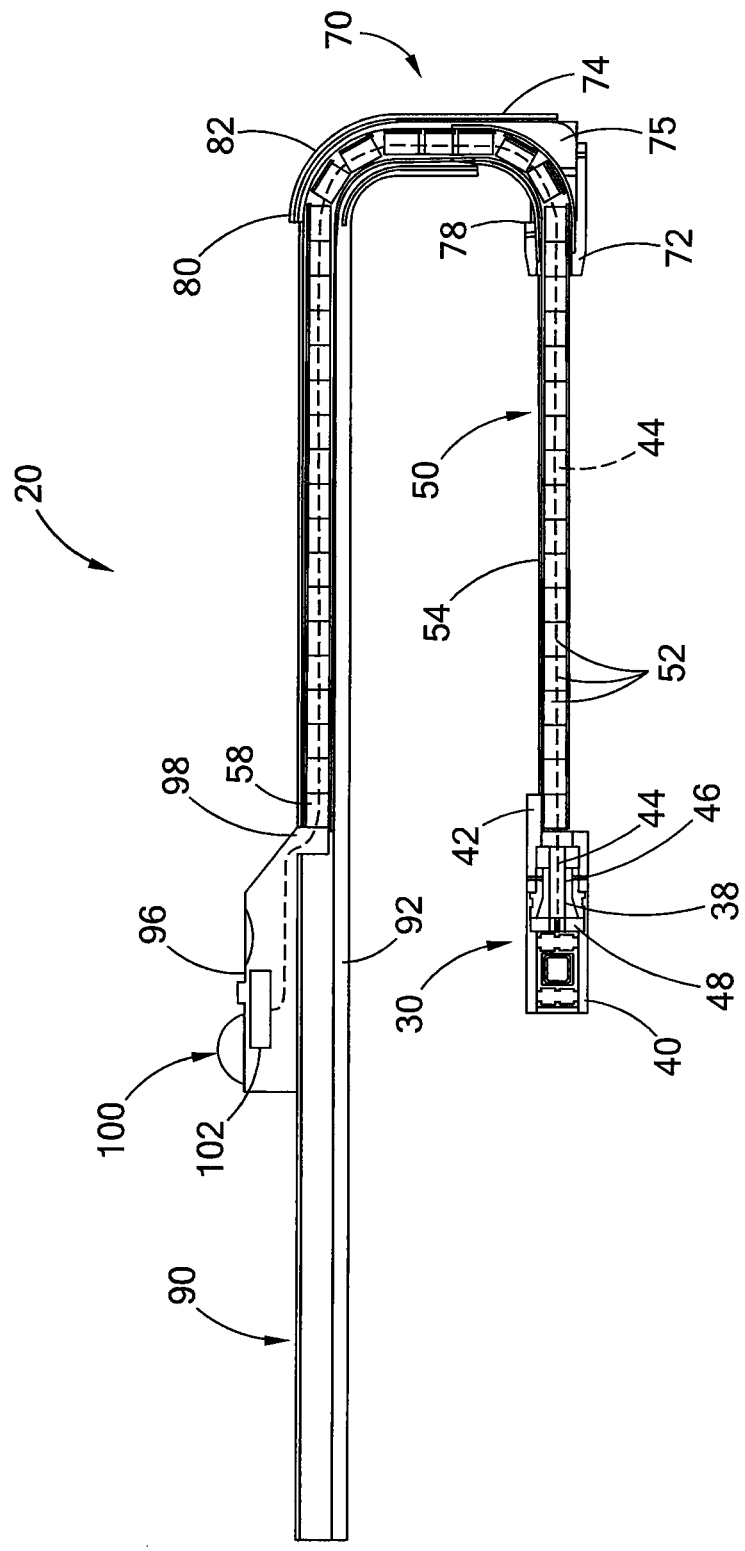
FIG. 3 is a cross-sectional view of the medical system depicted in FIG. 2.

Turning now to the figures, FIGS. 1-3 depict a medical system 20 for use intracorporeally to assist in surgical procedures beneath a tissue layer 10. The tissue layer 10 is typically that of a mammalian patient having a skin layer covering an bodily cavity 12 such as the abdominal or thoracic cavity having various organs 18 (FIG. 11) therein. It will be readily apparent to those skilled in the art that the medical system 20 may be employed with many different bodily cavities and bodily structures, and is not limited to those described or depicted herein. The medical system 20 generally includes a distal portion 22 intended to be utilized beneath the tissue 10 and within the body cavity 12, and a proximal portion 24 intended to reside above the tissue 10 and controlled by the medical professional or other user.

In particular, the distal portion 22 of the medical system 20 generally includes a camera head 30 that is connected to a translating beam 50. The beam 50 slidably attaches through a guide sheath 70, part of which is also within the distal portion 22. The guide sheath 70 attaches to a handle 90 within the proximal portion 22 of the medical system 20, which is utilized to orient and control translation of the beam 50 and camera head 30. The medical system 20 is generally intended to be used in conjunction with a port 14 positioned within an opening 13 (FIG. 11) in the tissue 10. The port 14 has been depicted in FIG. 1 as a simple tubular member that is fitted within the opening 13, although various types of ports utilized in laparoscopic or other minimally invasive surgeries may be employed. One preferred port is that disclosed in U.S. Appl. No. 61/564,021 filed Nov. 28, 2011 entitled SURGICAL ACCESS PORT the contents of which are incorporated herein by reference in its entirety.

Through use of the medical system 20 the entire area of the bodily cavity 12 may be visualized while additional medical instruments may be employed through the port 14 or through other access points to perform minimally invasive surgeries. As will be described in more detail herein, the beam 50 is a one-way bending beam which can bend through the angles formed by the guide sheath 70 to allow the system 20 to rotate through the tissue 10 and extend generally in the plane of the tissue 10. The beam 50 resists bending in one direction and is oriented relative to the guide sheath such that, as the beam is slid relative to guide sheath, the beam bends in a first direction (generally down on the page in FIGS. 1-3) through the bends in the guide sheath 70, while a projecting portion of the beam (projecting from the distal end of the guide sheath) resists bending in a second direction opposite the first direction (generally up on the page in FIGS. 1-3). Stated another way, the beam 50 is a cantilevered beam that is supported at the distal opening of the guide sheath 70. The beam 50 resists bending 'downward' under the force of gravity, assuming the system 20 and beam 50 are oriented appropriately relative to gravity, e.g. in most abdominal surgeries where the patient is in a supine or semi-supine position. However, the skilled artisan will recognize that the system 20 may be utilized when the patient is in other positions or the system 20 and beam 50 are rotated such that the plane of the first and second directions is not perfectly perpendicular to the ground.

The apparatus 20, and in particular the handle 90 and guide sheath 70, may also be rotated relative to the port 14 such that the distal portion 22 and its camera head 30 sweep through a plane generally parallel to the tissue 10. Further, the beam 50 may be extended and retracted distally and proximally to position the camera head 30 within the cavity 12. Additionally, the camera head 30 pivots relative to the beam 50, and preferably provides for both rotation about an axis 16 defined by the beam 50 as well as pivoting about an axis transverse to the axis of the beam 50. Accordingly, the medical system 20 provides 4 degrees of freedom to the camera head 30 for improved visualization and lighting throughout the body cavity 12.

Turning now to FIG. 2, the camera head 30 generally includes a camera 32 and one or more lighting elements 34. Additional elements such as an electro cautery device 36 or injection ports may be provided within the camera head 30. Preferably, the camera 32 is an HD camera which utilizes laparoscope camera technology having rod-lens imaging and "chip-in-the-tip" imaging. Utilizing rod-lenses, the images from the cameral 32 are captured on a sensor within the camera head 30 or within the handle 90. The lighting elements 34 are preferably LED elements and provide illumination via a electrical connection with the handle 90, or are lenses connected to a fiber optic cable carrying light from an external lamp, such as a Xenon arc lamp.

The camera head 30 generally includes a joint member 38 connecting a distal head portion 40 to a proximal head portion 42. The joint 38 is pivotally connected to the proximal head portion 42, e.g. via a pin, ball-and-socket or other pivotal connection, to allow the joint 38 and the distal head portion 40 to pivot relative to the proximal head portion 42 and beam 50. The joint 38 also provides a flange 48 defining a surface about which the distal head portion 40 may rotate about the longitudinal axis of the joint 38 (and often axis 16 as shown). The pivoting and rotation of the camera head 30 may be accomplished via appropriately located control wires 44 which pass through an interior passageway 46 of the joint 38 and through the interior of the beam 50. The control wires 44 may mechanically transfer energy to the camera head 34 for articulation, or the camera head 30 may include small motors or prime movers (not shown) that are electrically driven via electric control wires 44.

Figure 4:
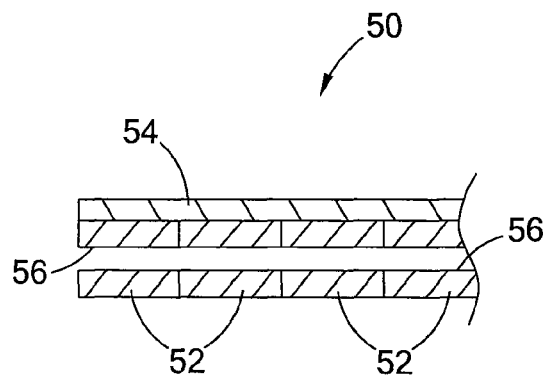
FIG. 4 is a cross-sectional view, partially cut-away or a beam forming a portion of the medical system depicted in FIGS. 1-3.
Figure 4A:
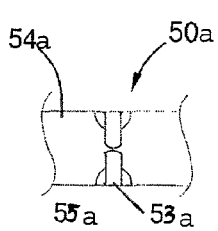
FIG. 4a is a top view of an alternate of the beam of FIG. 4.

As also shown in FIGS. 2 and 3, the beam 50 is generally formed by a plurality of links 52 connected on one side by a flexible strip 54. As best seen in FIG. 4, each of the links 52 preferably includes a bore 56 which is aligned with adjacent bores 56 to form an internal passageway through the beam 50 leading between the camera head 30 and the handle 90. One or more links 52 at the distal end of the beam 50 is attached to the proximal head portion 42 of the camera head 30. The links 52 may be formed of plastic or metal, while the strip 54 is formed of a resilient but flexible material, preferably of nitinol or other biocompatible metal or alloy, although sufficiently resilient plastics can also be used. The flexible strip 54 may be attached to the links 52 via an adhesive or using other bonding techniques such as fusion, soldering or welding at appropriate points to provide one-way bending. For example, the strip 54 may include lateral slots, preferably at axial positions spaced from the abutting corners of the links, to provide a location for soldering or to control the stiffness and flexibility of the strip 54. Likewise, as shown in FIG. 4a, the links may be attached to the strip 54a by bending small tabs 53a formed in the links, namely bending the tabs 53a through the lateral slots 55a and over the strip 54a thereby locking the links in place.

Figure 5:
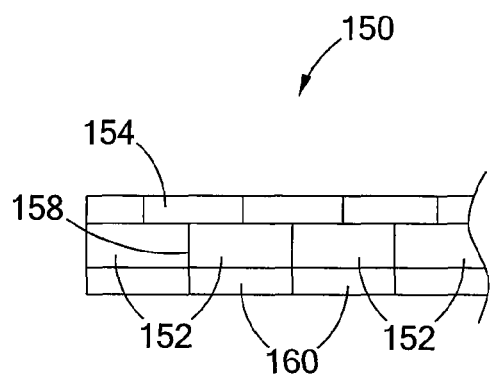
FIG. 5 is a side view, partially cut-away of an alternate embodiment of the beam depicted in FIG. 4.

It will be recognized by the skilled artisan, in view of this disclosure, that other variations of the beam 50 are possible to provide for a one-way bending beam which allows bending in a first direction (i.e. towards one side of the beam) so that it may pass through the bends formed in the guide sheath 70 as shown in FIGS. 2 and 3, while resisting bending in a second direction opposite the first direction so that the beam 50 may be extended distally from the guide sheath 70 as also shown in FIGS. 2 and 3. Preferably, the beam 50 does not flex more than 1 to 10 degrees from the straight linear axis 16 depicted in the figures. For example, in FIG. 5 an alternate beam 150 (shown from the side) includes a plurality of links 152 which are connected to a plurality of small strips 154. The plurality of strips 154 are positioned to extend over the abutting corners 158 defining by the abutting surfaces 160 of adjacent links 152. As in the prior embodiment, the plurality of strips 154 are flexible such that the lower corners 162 (i.e. those down on the page in FIG. 5) may move away from each other while the links 152 general pivot about the other edges 158 which are held together via the strips 154.

Figure 6:
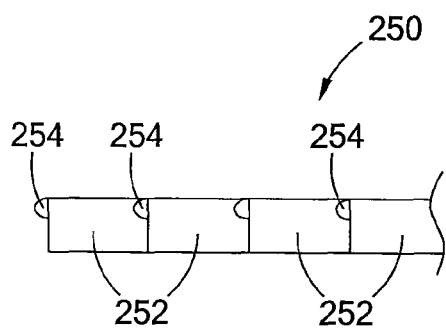
FIGS. 6 and 7 are side views, partially cut-away of another alternate embodiment of the rail and yet another alternate embodiment of the rail depicted in FIG. 5.
Figure 7:
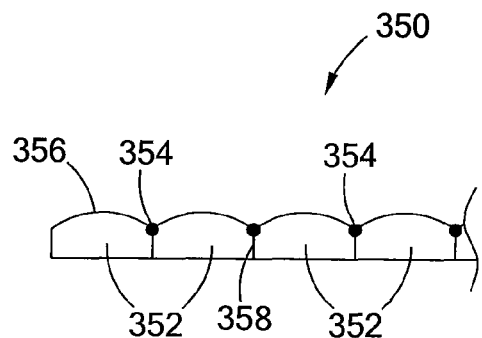

In FIG. 6, an alternate beam 250 includes a plurality of links 252 that are pivotally connected together at their upper adjacent corners via corresponding tabs and detents 254 which provide a hinge joint. Similarly, FIG. 7 depicts an alternate beam 350 which includes a plurality of links 352 and each are pivotally attached at their upper corners to pins 354 which allow the links 352 to rotate relative to one another about the pins 354. Here the corners of the upper surfaces 356 are rounded (or chamfered, filleted, etc.) to accommodate the rotation, while the links include adjacent abutting surfaces 358 which extend below the pins 354 to prevent bending in the opposite direction (i.e. down on the page).

Turning back to FIG. 2, the guide sheath 70 is tubular and generally includes a first sheath portion 72 and a second sheath portion 74. The first sheath portion is straight and defines a first axis (shown as coincident with axis 16 in FIG. 2), and likewise the second sheath portion 74 is generally straight and defines a second bend 75. The first sheath portion 72 is rotatable relative to the second sheath portion 74 about a hinge 76 to adjust the angle between the first and second axes. A control wire or other control member (not shown) is attached to the first sheath portion at a position distal to the hinge 76 to control articulation of the first sheath portion 72 between an introduction configuration and an operative configuration. In the introduction configuration (FIG. 8) the first sheath portion 72 is generally aligned with the second sheath portion 74 such that the first axis and second axis are generally parallel. In the operative configuration (FIGS. 2, 3, 9) the first axis is rotated relative to the second axis, preferably between 1 and 135 degrees and most preferably around 90 degrees. FIG. 2 also shows that the first sheath portion 72 preferably includes plurality of projecting tabs 73 in an area of the hinge connection that are angularly spaced. The tabs 73 are sized and positioned to engage the second sheath portion 74 (or are otherwise operatively connected thereto) to provide for discrete angular positioning of the first sheath portion 72 relative to the second sheath portion 74.

In the operative configuration shown in FIG. 2, it can be seen that a recess 78 is formed in the first sheath portion 72 and a corresponding recess (not shown) in the second sheath portion 74 provides an open space for the beam 50 to pass through a first bend 75 formed between the first and second sheath portions 72, 74. A third portion 80 of the guide sheath 70 (at a proximal end thereof) further defines a second bend 82. The second bend is fixed, such as by rigidly joining or unitarily forming the second and third sheath portions 74, 80, and is preferably around 90 degrees. Optionally the second bend could also be a controllable pivoting joint.

Accordingly, in the operative configuration shown in FIGS. 2 and 3, the beam 50 rotates about 90 degrees through the second bend 82, and then rotates another 90 degrees through the first bend 75 such that a distal portion of the beam 50 extends generally parallel to a proximal portion of the beam 50 that is external to the tissue 10 (as with the distal and proximal portions 22, 24 of the system 20 described above).

As also seen in FIGS. 2-3, a proximal end 58 of the beam 50 is attached to the handle 90. As best seen in FIG. 2, the handle 90 generally includes a housing 92 defining a guide rail 94, which has been depicted as a simple slot 94 formed longitudinally through the housing 92. A thumb slider 96 slides along the housing 92 guided by the slot 94, and includes a tab 98 projecting through the slot 94 and riding within the housing 92. The tab 98 is attached to the proximal end 58 of the beam 50, i.e. to one or more proximal links 52. Through translation of the thumb slider 96, the beam 50 may be moved distally and proximally through the guide sheath 70 and within the body cavity 12. The control wires 44 extending from the camera head 30 through the beam 50 also extend through the thumb slider 96 to various controls 100 located on thereon. The controls 100 may be operatively connected to a circuit board 102 or other electronic elements for transmitting and storing signals from the camera head 30, or may be attaching to winding wheels, torque wheels, tensioning mechanisms and the like for transmitting mechanical energy through the control wires 44 (e.g. for rotation of the camera 32).

Figure 8:
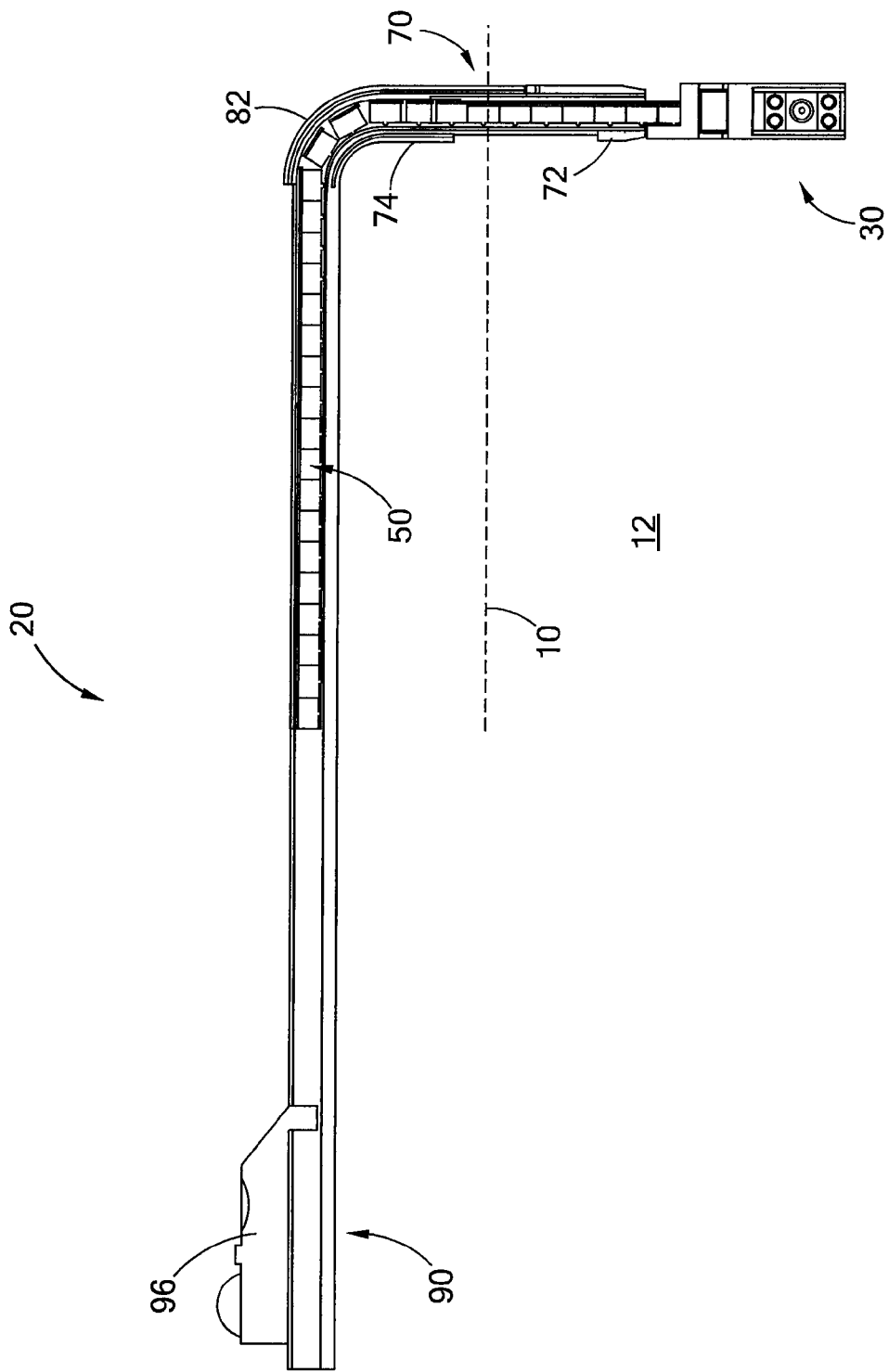

Turning now to FIGS. 8-10, operation of the medical system 20 will be described. In FIG. 8 the medical system 20 is shown in the introduction configuration where the thumb slider 96 of the handle 90 is moved proximally (to the left on the page) to retract the beam 50. The beam 50 extends through the second bend 82 of the guide sheath 70 and through both the first and second sheath portions 72, 74 which are generally parallel. It will be recognized that the angle of the second bend 82, the angle of the first bend 75 (which can be greater than zero in the introduction configuration), and the size of the first and second sheath portions 72, 74 are configured relative to one another to allow the distal portion 22 of the medical system 20 to pass through the opening in the port 14 (or directly through the opening 13 in tissue 10).

After the camera head 30 and first sheath portion 72 are passed through the port 14 (or otherwise through the tissue 10), the first sheath portion 72 may be rotated relative to the second sheath portion 74 such that the guide sheath 70 forms the first bend 75, as shown in FIG. 9. Rotation of the first sheath section 72 causes the distal end of the beam 50 to be rotated a total of about 180 degrees relative to the proximal portion residing in the handle 90. In this position, the entire handle assembly 90 may be rotated about a plane of the tissue 10 and the camera head 30 rotated or pivoted to initially identify the structures within the cavity 12.

Figure 11:
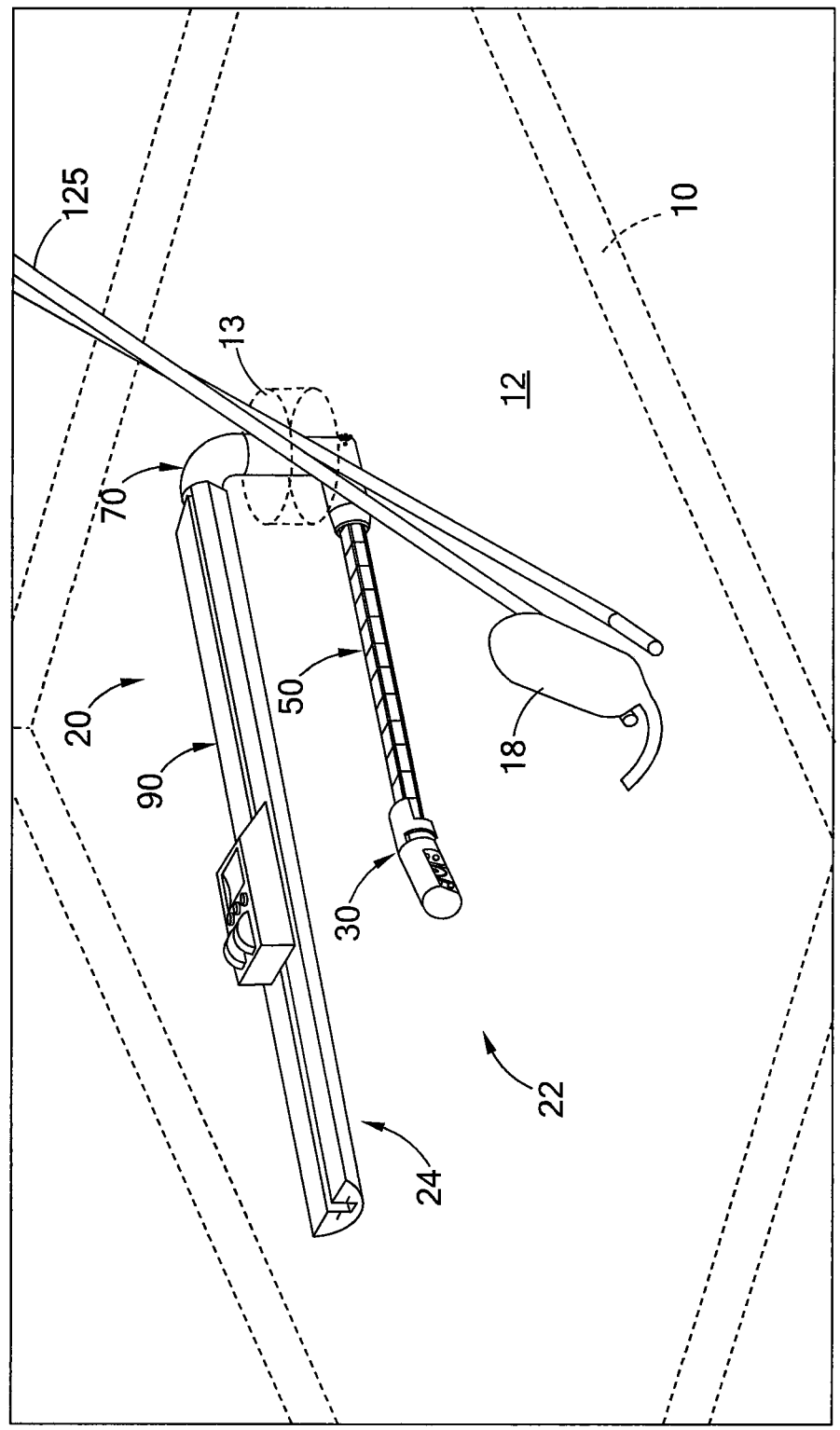
FIG. 11 is a perspective view showing operation of the medical system depicted in FIGS. 1-3.

Through translation of the thumb slider 96 relative to the housing 92 of the handle 90, the beam 50 may be slid through the guide sheath and distally projected as shown in FIG. 10. The beam 50 and camera head 30 project beyond a distal end of the guide sheath 70 and further into the cavity 12. As shown in FIG. 11, upon securing ideal lighting and visualization of the target within the cavity 12, additional instruments 125 may be passed through the port 14 or through other access points into the cavity 12 for performing surgery such as a laparoscopic or other minimally invasive surgery. Accordingly, it can be seen that the medical system 20 provides a means for introducing a distal section 22 of the device within the bodily cavity 12 while a proximal portion of the device 24 remains above the tissue 10 while the two portions 22, 24 are generally parallel to one another. This configuration is relatively unobtrusive to other instruments, and provides complete viewing of the cavity 12 by providing the camera 32 with 3 or 4 degrees of freedom. One of the advantages of the system 20 is that the camera 30 is moved away from the immediate vicinity of the operating field and other instruments, so that the instruments may be viewed from a side-view rather than head-on. This is likely to be an ideal perspective for operative visualization.

While the guide sheath 70 is generally depicted as performing a U-turn or bend in the operative configuration, it will be recognized that the pivotal connection between the first and second sheath portions 72, 74 can be such that the beam 50 is not coplanar with the handle 90 or the portion of the beam therein, or such that the beam 50 follows one or more bends that form an S-shape or Z-turn. In the operative configuration depicted in FIG. 11, the camera head 30 is provided with 4 degrees of freedom to find the best position within the cavity 12 to navigate around adjacent structures to illuminate and visualize an organ or other bodily structure 18 within the cavity 12, while still providing sufficient space for additional medical instruments 125 to be inserted through the opening 13 and the tissue 10 for operation on the same bodily structure 18. The articulation of the camera head 30 allows any degree of triangulation between the additional instruments and the camera head pointing towards the target. Accordingly, the medical system 20 is especially adapted for minimally invasive surgery which utilizes a single incision or single port.

Preferably, the camera head 30 includes side viewing camera 32, although it can also be provided at the distal end of the distal head portion 40. It will also be recognized that control wires 44 need not extend through the beam 50, and could be provided alongside the exterior of the beam 50 such that the plurality of links 52 may be solid. In some embodiments, the thumb slider 96 could be motorized, and further be electrically connected to a computer with proper software to control articulation of the slider 96 and translation of the beam 50, as well as both mechanical and electrical control over camera head 30 and receipt of its visual information.

It will also be recognized by those skilled in the art that, while the methods described above generally include passing through tissue and into an internal bodily cavity or lumen, it will be recognized that the systems, devices and methods may be used on any layer of material (e.g. fabrics, cloth, polymers, elastomers, plastics and rubber) that may or may not be associated with a human or animal body and a bodily lumen. For example, the systems, devices and methods can find use in laboratory and industrial settings for placing devices through one or more layers of material that may or may not find application to the human or animal body, and likewise closing holes or perforations in layers of material that are not bodily tissue. Some examples include viewing behind structures such as walls, plates, floors, rubble (e.g. in rescue work), as well as working with synthetic tissues, polymeric sheets, animal studies, veterinary applications, and post-mortem activities.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical system for use intracorporeally to assist in surgical procedures beneath a tissue layer, the system comprising:
   a camera;
   a beam having a distal end attached to the camera, the beam bendable in a first direction and resisting bending in a second direction opposite the first direction;
   a guide sheath slidably receiving the beam, the beam extending through a distal end of the guide sheath such that the camera projects from the distal end of the guide sheath, the guide sheath including a first sheath portion defining a first axis and a second sheath portion defining a second axis, the guide sheath having an operative configuration wherein the first sheath portion is angled relative to the second sheath portion to define a first bend, a third sheath portion angled relative to the second portion to define a second bend; and
   the beam structured and oriented relative to the guide sheath such that, as the beam is slid relative to guide sheath, the beam bends in the first direction through the first bend, and a projecting portion of the beam projecting from the distal end of the guide sheath prevents substantial bending in the second direction.

2. The medical system of claim 1, wherein the beam sufficiently resists bending such that it does not bend under its own weight and the weight of the camera.

3. The medical system of claim 1, wherein the beam sufficiently resists bending such that the projecting portion of the beam defines a beam axis extending linearly from the distal end of the guide sheath.

4. The medical system of claim 1, wherein the beam is hollow to define a passageway extending to the distal end of the beam, and further comprising a control wire extending through the passageway and operatively connected to the camera.

5. The medical system of claim 1, wherein the first bend is formed by the first sheath section being angled about 90 degrees relative to the second sheath section.

6. The medical system of claim 1, wherein the first sheath section is rotatably attached to the second sheath section.

7. The medical system of claim 6, wherein the guide sheath has an introduction configuration wherein the first sheath section is generally parallel to the second sheath section.

8. The medical system of claim 1, wherein the first sheath section is operable to rotate relative to the second sheath section over an arc spanning about 90 to about 135 degrees.

9. The medical system of claim 1, wherein the second bend is at a fixed angle.

10. The medical system of claim 1, wherein the first and second bend are oriented in the operative configuration to bend the beam over 180 degrees such that a proximal beam portion is about parallel to a distal beam portion.

11. The medical system of claim 1, further comprising a camera head supporting the camera and attached to the distal end of the beam, wherein the camera head includes a proximal head portion fixed to the beam and a distal head portion rotatably attached to the proximal head portion.

12. The medical system of claim 11, wherein the distal head portion rotates about a pivot axis such that the distal head portion is angled relative to the proximal head portion.

13. The medical system of claim 12, wherein the pivot axis is perpendicular to a longitudinal axis of a projecting portion of the beam that projects from the guide sheath.

14. The medical system of claim 11, wherein the distal head portion rotates about a pivot axis, the pivot axis about parallel to a longitudinal axis of a projecting portion of the beam that projects from the guide sheath.

15. The medical system of claim 14, further comprising an intermediate head portion interconnecting the proximal and distal head portions, wherein the intermediate head portion is rotatable relative to one of the proximal and distal head portions about a first pivot axis such that the distal head portion is angled relative to the proximal head portion, and wherein the intermediate head portion is rotatable relative to other of the proximal and distal head portions about a second pivot axis that is about parallel to a longitudinal axis of a projecting portion of the beam that projects from the guide sheath.

16. The medical system of claim 1, further comprising a port positionable within the tissue layer, wherein the guide sheath has an introduction configuration wherein the first sheath portion is angled between about 0 degrees and 135 degrees relative to the second sheath portion and sized such that the first sheath portion may pass through the port such that the beam extends from a first side of the tissue layer to a second side of the tissue layer opposite the first side.

17. The medical system of claim 1, wherein the beam is structured such that the projecting portion of the beam always prevents substantial bending in the second direction.

18. The medical system of claim 1, wherein adjacent links are directly hinged together at their ends on a first side facing the first direction, and wherein the plurality of links each include second end surfaces spaced in the second direction from the first side, wherein second end surfaces of adjacent links abut each other.

19. A medical system for use intracorporeally to assist in surgical procedures beneath a tissue layer, the system comprising:
   a camera;
   a beam having a distal end attached to the camera, the beam bendable in a first direction and resisting bending in a second direction opposite the first direction;
   a guide sheath slidably receiving the beam, the beam extending through a distal end of the guide sheath such that the camera projects from the distal end of the guide sheath, the guide sheath including a first sheath portion defining a first axis and a second sheath portion defining a second axis, the guide sheath having an operative configuration wherein the first sheath portion is angled relative to the second sheath portion to define a first bend;
   the beam structured and oriented relative to the guide sheath such that, as the beam is slid relative to guide sheath, the beam bends in the first direction through the first bend, and a projecting portion of the beam projecting from the distal end of the guide sheath prevents substantial bending in the second direction; and
   a handle attached to the guide sheath.

20. The medical system of claim 19, wherein the beam is formed by a plurality of links connected together for relative rotation between adjacent links, and wherein the links forming the projecting portion are structured to be incapable of rotating in the second direction relative to adjacent links.

21. The medical system of claim 20, wherein the links are connected by at least one bendable strip attached to each link on the first side of each link.

22. The medical system of claim 20, wherein the links include tabs pivotally connected to an adjacent link.

23. The medical system of claim 20, wherein, when the beam extends in a straight line, the end surfaces include abutting portions positioned away from the first side towards the second direction.

24. The medical system of claim 19, wherein the first sheath section is rotatable relative to the second sheath section, and wherein the beam is hollow to define a passageway extending to the distal end of the beam, and a further comprising a sheath control wire extending through the passageway and operatively connected to the first sheath section.

25. The medical system of claim 24, wherein the camera head includes a proximal head portion fixed to the beam and a distal head portion rotatably attached to the proximal head portion, and further comprising a camera control wire extending through the passageway of the beam operatively connected to the camera head.

26. The medical system of claim 24, wherein at least two of mechanical, electrical and optical control wires extend through the passageway of the beam for operation of the camera head.

27. The medical system of claim 19, wherein the handle includes a handle housing and a control slider slidably attached thereto, the control slider attached to the beam for translation of the beam through the guide sheath to position the camera head relative to the guide sheath.

28. The medical system of claim 19, wherein the beam is structured as a one-way bending beam and is incapable of bending substantially in the second direction.

29. The medical system of claim 19, wherein the beam is formed by a plurality of links connected together for relative rotation between adjacent links, and wherein the links include a first side facing the first direction, and a second side facing the second direction, and wherein adjacent links are pivotally connected together about a pivot point located at their respective first sides.

* * * * *